US009517166B2

(12) United States Patent
Kabadayi

(10) Patent No.: US 9,517,166 B2
(45) Date of Patent: Dec. 13, 2016

(54) DEVICE AND METHOD FOR CONTROLLING NASAL EXUDATION

(76) Inventor: Cihan Kabadayi, Obertrum am See (AT)

(*) Notice: Subject to any disclaimer, the term of this patent is extended or adjusted under 35 U.S.C. 154(b) by 815 days.

(21) Appl. No.: 13/510,247

(22) PCT Filed: Nov. 16, 2010

(86) PCT No.: PCT/EP2010/006970
§ 371 (c)(1),
(2), (4) Date: Sep. 12, 2012

(87) PCT Pub. No.: WO2011/057823
PCT Pub. Date: May 19, 2011

(65) Prior Publication Data
US 2012/0330344 A1   Dec. 27, 2012

Related U.S. Application Data

(60) Provisional application No. 61/283,754, filed on Dec. 8, 2009.

(30) Foreign Application Priority Data

Nov. 16, 2009   (EP) .................................... 09014311
Dec. 8, 2009    (EP) .................................... 09015221

(51) Int. Cl.
*A61M 29/00*   (2006.01)
*A61F 13/20*   (2006.01)
*A61F 13/00*   (2006.01)

(52) U.S. Cl.
CPC ....... *A61F 13/2005* (2013.01); *A61F 13/2022* (2013.01); *A61F 13/204* (2013.01);
(Continued)

(58) Field of Classification Search
CPC . A61M 29/00; A61M 29/02; A61B 17/12022; A61B 17/12099; A61B 17/1219; A61B 17/12104; A61B 17/12136; A61F 13/20; A61F 13/2002; A61F 13/2005; A61F 13/2031; A61F 13/204; A61F 13/207; A61F 13/2074; A61F 13/2077; A61F 13/208; A61F 13/42
See application file for complete search history.

(56) References Cited

U.S. PATENT DOCUMENTS 2,847,997 A * 8/1958 Tibone ............. A61B 17/12104
                                                        604/104
3,903,893 A * 9/1975 Scheer .......................... 606/196
(Continued)

FOREIGN PATENT DOCUMENTS

WO   WO 2011002357 A1 * 1/2011 ............. A61F 13/20

OTHER PUBLICATIONS

International Search Report issued in corresponding International application No. PCT/EP2010/006970, mailing date Mar. 28, 2011.
(Continued)

*Primary Examiner* — Robert Lynch
(74) *Attorney, Agent, or Firm* — Patent Portfolio Builders PLLC

(57) ABSTRACT

An inflatable device for insertion into a user's nose for controlling nasal exudation has an elongated shaft including at least one lumen for accommodating a fluid (15); an inflatable balloon (25) connected to the shaft, the balloon (25) being in fluid connection to the lumen; and an absorber (19, 33) for absorbing nasal exudates, the absorber (19, 33) being disposed at an outer circumference of the shaft and/or at a distal tip portion (9) of the device. Another inflatable device for insertion into a user's nose for controlling nasal exudation has an elongated shaft including at least one lumen for accommodating a fluid (15); and an inflatable balloon (25) connected to the shaft, the balloon (25) being in fluid connection to the lumen; the balloon (25) containing
(Continued)

a cooling agent (29), wherein the cooling agent (29) is configured to cool the balloon (25) when coming into contact with the fluid (15).

17 Claims, 2 Drawing Sheets

(52) U.S. Cl.
CPC ......... *A61F 13/208* (2013.01); *A61F 13/2074* (2013.01); *A61F 13/2077* (2013.01); *A61F 2013/00468* (2013.01)

(56) References Cited

U.S. PATENT DOCUMENTS

| | | | |
|---|---|---|---|
| 5,011,474 A | | 4/1991 | Brennan |
| 5,383,891 A | | 1/1995 | Walker |
| 6,248,092 B1 | * | 6/2001 | Miraki ................. A61M 25/00 604/905 |
| 2006/0074397 A1 | * | 4/2006 | Shimada ....................... 604/509 |
| 2007/0078366 A1 | * | 4/2007 | Haggstrom ......... A61F 13/0203 602/53 |
| 2007/0239110 A1 | * | 10/2007 | Shah ........................ 604/96.01 |
| 2009/0259173 A1 | | 10/2009 | Wang |
| 2010/0312338 A1 | * | 12/2010 | Gonzales ............... A61B 17/24 623/10 |

OTHER PUBLICATIONS

Written Opinion of the International Searching Authority issued in International application No. PCT/EP2010/006970, mailing date Mar. 28, 2011.

\* cited by examiner

DEVICE AND METHOD FOR CONTROLLING NASAL EXUDATION

BACKGROUND OF THE INVENTION

This invention relates generally to the controlling of nasal exudation, and more particularly to a device and method therefore.

Nasal exudation is a common phenomenon. One of the more common methods of arresting such exudation is to insert an absorbing packing material into the nasal cavity. A large percentage in the order of 90% of all nose bleeds, which are a particularly unpleasant or even dangerous kind of nasal exudation, occur within the location of the vascular plexus which is located in the forward areas of the nasal cavity on the nasal septum or nasal partition. The various networks of arteries, minute blood vessels and caplillaries in this area are the most common source of nose bleeds or nasal hemorrhages.

There are various home remedies for simple nose bleeds such as cold compresses to the neck, manually compressing the nostrils along with various other techniques, none of which are particularly effective since the actual site of the exudation (here, bleeding) is within the nasal cavity. Nose bleeds in this forward area of the vascular plexus commonly referred to as the Kiesselbach plexus, are relatively easy to control by a non-physician because of their ready accessibility and because the affected area can be visually ascertained.

A pre-packaged nose bleed kit sold across the counter for home use, as known from U.S. Pat. No. 5,383,891, includes a hemostatic tampon construction of a compressed synthetic hydrocellulose sponge material which expands upon wetting, and a nasal bandage which provides an absorbent drip pad under the nostrils as well as some means for anchoring a pull string of the tampon. This kit is still not sufficiently effective, and is not sufficiently readily applicable.

SUMMARY OF THE INVENTION

The present invention, according to its first aspect, is an inflatable device for insertion into a user's nose for controlling nasal exudation, the device comprising a shaft accommodating a fluid, and a balloon connected or connectable to the shaft so as to be in fluid connection therewith. The balloon is inflatable by the fluid contained in the shaft, so as to exert pressure on the walls of the nasal cavity after the distal portion of the device has been inserted thereinto.

According to an embodiment, an absorber for absorbing nasal exudates is disposed at an outer circumference of the shaft. This absorber may comprise a section which remains visible after insertion. Further, the shaft may comprise at least one mark for indicating an amount of nasal exudates absorbed.

According to another embodiment, an absorber for absorbing nasal exudates is disposed at a distal tip portion of the device. In this case, the absorber may constitute the entire distal tip section apart from a support structure for the absorber. A length of the distal portion including the balloon and the tip-absorber may be limited to at most 5 cm.

The above embodiments may be combined, such that there are absorber sections as well at the tip section as around the shaft. In embodiments where the balloon does not extend around the entire circumference, but only partially or for the most part of the circumference, such as in a case where there are two distinct balloon sections, the two absorber sections may be contiguous. Additionally, some absorber material may be disposed on the outer surface of the balloon itself.

According to another embodiment, the balloon contains a cooling agent. In this embodiment, the cooling agent may be configured to dissolve in the liquid accommodated until use in the shaft's lumen. If an enthalpy of solution in the solvent is positive, cooling of the balloon will result upon contact.

The device may comprise a valve, or a rupturable membrane, e.g. to keep the solvent and the cooling agent separate until use. The shaft may contain a plunger, with which the fluid or solvent can be urged into the balloon so as to inflate it, rupturing the membrane (if provided) or passing through the valve (if provided) on its way. The embodiment comprising the cooling agent may be combined with either or both embodiments comprising the additional absorber outlined above.

According to another aspect, a method of controlling nasal exudation comprises introducing an inflatable balloon into a (conscious) user's nose, inflating the balloon, and internally cooling the balloon so as to reduce nasal exudation. By "internally" it is meant that the cooling is not achieved by e.g. flowing a pre-cooled fluid through the device; nor by applying pre-cooled packaging to the outside of the nose. The cooling may be achieved by dissolving a suitable agent in a solvent wherein the agent has a positive enthalpy of solution. The solvent, before contacting the cooling agent, may be urged through a constriction like a valve or a rupturable membrane.

According to yet another aspect, a cooling agent having a positive enthalpy of solution in a solvent is used in the manufacturing of a device for controlling nasal exudation. Both the solvent and the solute (agent) are arranged in the device, such that in operation, the agent dissolves in the solvent, thereby cooling the device and accordingly the nose.

While in the above description, it has been assumed that the device comprises an inflatable balloon connected to a shaft, these components may likewise be provided as separate items. It is, e.g., possible to provide only the balloon, along with any optional absorber sections, which balloon for use may be connected to a fluid-filled syringe. In this case, the syringe provides the shaft and lumen required to inflate the balloon.

It is further conceivable to arrange a cooling agent initially outside the inflatable part of the balloon in such a manner that the agent, in use, first comes into contact with the fluid, e.g. water, dissolves therein, and only then is urged into the inflatable part of the balloon so as to inflate it. For the purpose of this description, such structure will be considered part of the invention insofar as before use, the agent and the fluid are kept separate, and in use, the cooling solution is contained in the inflated balloon.

Further advantages of the invention will become apparent from the following description and the accompanying drawings. These shall not be construed as limiting, the invention being solely defined by the appended claims.

DESCRIPTION OF THE PREFERRED EMBODIMENTS

Figure 1:
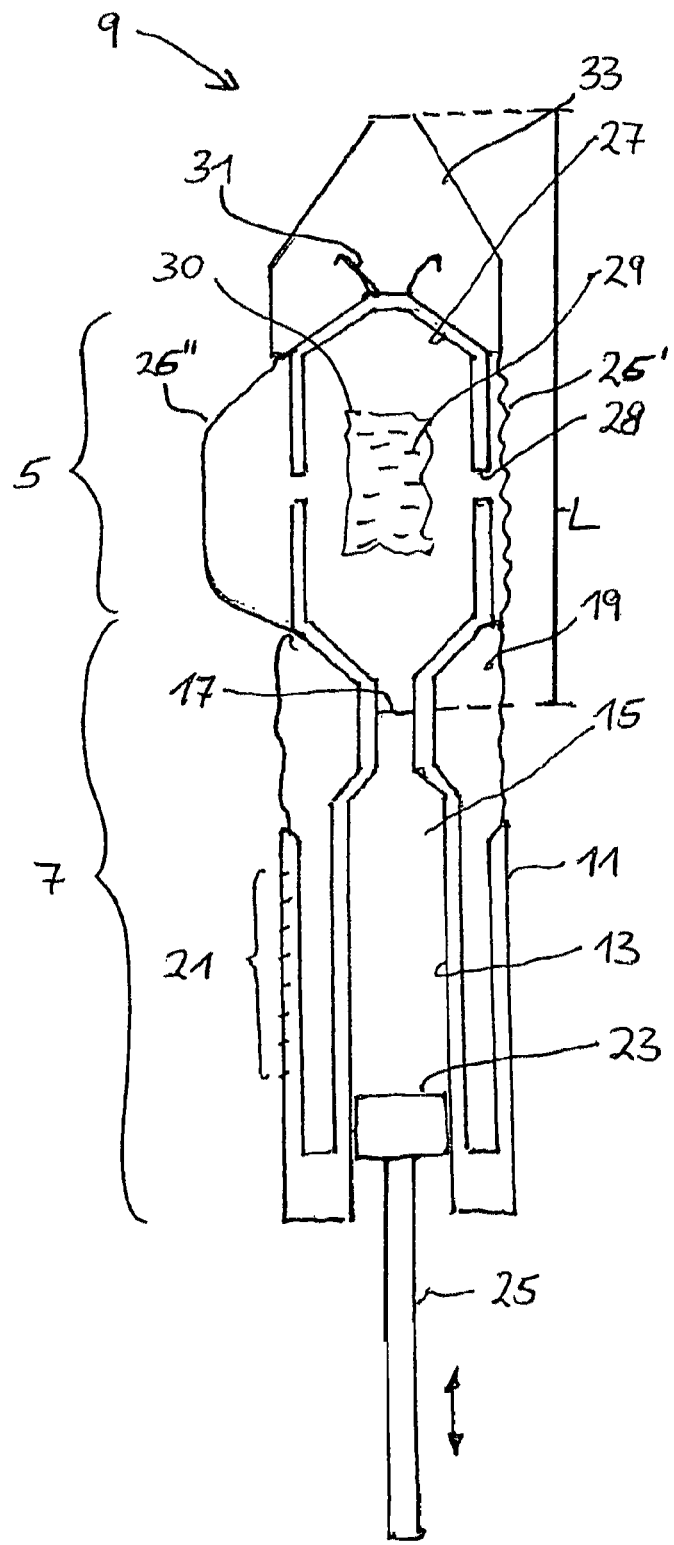
FIG. 1 shows a cross sectional view of the inventive device.

In the embodiment according to FIG. 1, the device comprises a body portion 7 having a cylindrical outer wall 11, a likewise cylindrical inner wall 13, accommodating water as the fluid 15 in its section below (proximal to) the septum 17, and an absorber 19 arranged in part between the outer 11 and inner 13 walls, and for another part around that section of the body 7 housing the septum 17. A part of the outer wall 11 is trans-parent, and bears marks forming a scale 21, for indicating progress of nasal exudates being absorbed by the absorber. For this purpose, the absorber 19 may contain an indicator agent if the nasal exudates are colorless (not necessary for blood).

A plunger 23, actuated via a plunger rod 25, defines a lumen of the shaft, wherein the plunger may be moved in the lengthwise direction indicated by the double-tipped arrow; namely, inwardly (upward in FIG. 1) when activating the device, and outwardly (downward in FIG. 1) before removing the device from the nose after use.

In the embodiment shown, the device's body 7 is contiguous with a balloon section 5 arranged distally of the body 7, which balloon section comprises the inflatable balloon 26. On the right hand side of FIG. 1, the balloon is shown in its normal, non-inflated state 26'; whereas on the left-hand side of FIG. 1, the balloon is shown in its inflated state 26". The balloon section 5 further comprises a chamber having a chamber wall 27 inside the balloon 25. The chamber wall 27 has openings 28 formed therein, for allowing an inflating fluid to pass therethrough, and ultimately to exert a pressure on the balloon 26 from the inside thereof. Inside the chamber, an agent 29 such as potassium nitrate ($KNO_3$) or the like is accommodated, which agent will readily dissolve in water (or other suitable fluid) under cooling when brought into contact. The agent may be provided in a small bag 30 made of a fluid permeable or perforated material, or a material disintegrating when brought into contact with the fluid. It is envisaged that the material of the bag will present some resistance to the ingress of water, so that the dissolving of the cooling agent will take some time, e.g. between 2 and 20 minutes, or between 5 and 10 minutes,. in order that the cooling will proceed in a smooth manner, avoiding undesirable freezing of the water.

Usually, around 2 ml will be sufficient to inflate the balloon 26. For children, less than that may be required; accordingly, a suitable volume of the lumen will generally be between 1 ml and 5 ml.

Although not shown, a connector arrangement may be provided at the distal end of the shaft, in order to assemble the body to the balloon section 5 described above. In this case, the septum 17 may comprise two septa in succession, wherein one septum forms part of the body section 7 (or syringe) and the other septum forms part of the balloon section 5, for sealing the balloon 26 until use. The connector assembly may consist of a male thread on the shaft part, and a matching female thread on the balloon part, or vice versa. It is envisaged to provide the various parts of the device, at least the shaft part including the plunger and the balloon part, as separate entities, which are assembled only immediately before use. The fluid may be provided in the shaft/plunger part, such as a syringe, or may be (tap or distilled) water to be filled into the lumen directly before use. In this variant, the plunger is initially in a position pushed inside the shaft, is drawn out of the shaft with the tip of the syringe held into a reservoir containing water (or into water flowing from a tap or the like) so as to suck water into the lumen of the syringe, and is then connected to the balloon part, ready for use. In another variant, it is envisaged to provide even the cooling agent separately. In this embodiment, the cooling agent may be configured to exert its cooling action upon being mechanically activated, such as pressed or bent. Such pressing or bending may trigger a transition from a meta-stable state into a stable state, the transition proceeding under cooling. The, activated cooling agent is then introduced into the balloon part, the shaft part connected thereto, the device inserted into the nostril and the balloon inflated. In this embodiment, it is not necessary that the process of dissolution proceeds under cooling, nor that the cooling agent dissolves in the fluid in the first place; rather, the fluid may merely serve as a heat conductor (from the nasal cavity wall into the balloon).

At the distal side of the chamber, a support arrangement such as two (or more.) hooks 31 for holding a further absorber 33 is located. The support arrangement 31 and the absorber 33 form a tip section. 9 of the device. The shape of the absorber 33 in this example is frustoconical or conical or egg-like, in order to facilitate insertion of the tip section 9 into the nostril.

Figure 3:
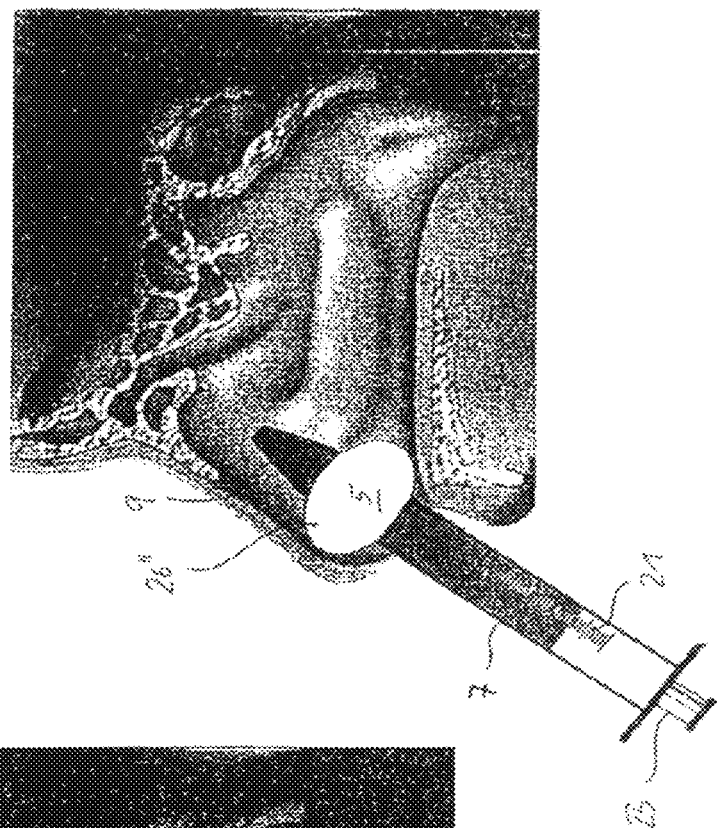
FIG. 3 shows a later phase of the inventive method.
Figure 2:
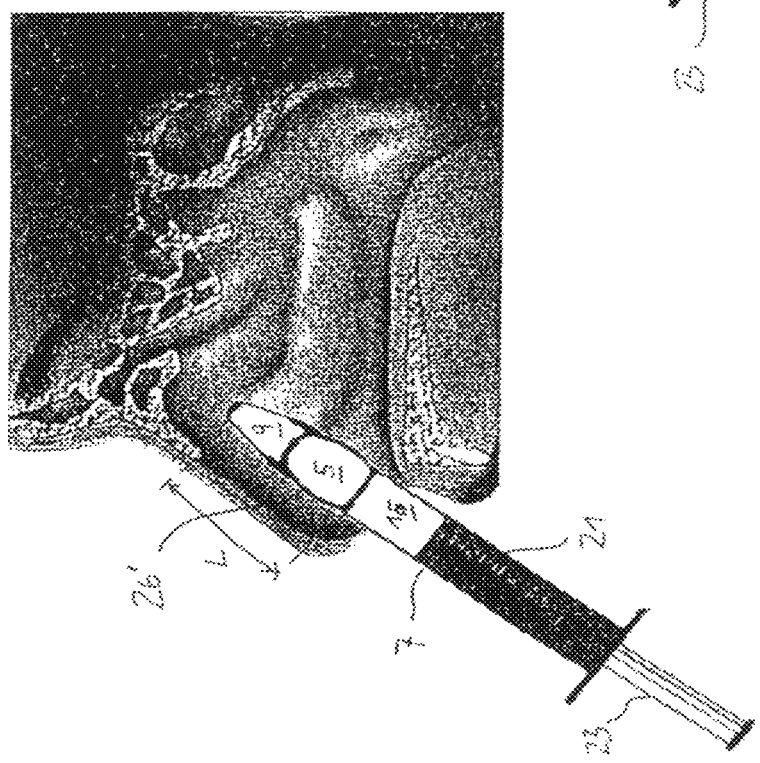
FIG. 2 shows an initial phase of the inventive method.

In operation, depicted in FIGS. 2 and 3, the device is farther inserted into the nostril, such that the balloon section 5 is likewise inside the nostril, but the scale 21 is outside thereof and still visible. At this stage, the balloon 26' is not yet inflated (FIG. 2). It may be seen that the length L of the device's balloon section 5 and tip section 9 combined is limited so as not to abut against the upper wall of the nasal cavity. In this embodiment, the length L is about 4 cm; generally, it will usually be in the range 3-5 cm.

After insertion, the plunger 23 is displaced inwardly so as to urge the fluid 15 contained in the lumen through the septum 17 and into the chamber (which in this embodiment accommodates the cooling agent 29). The fluid further exits the chamber through the openings 28 and thereby inflates the balloon 26", as shown in FIG. 3. The balloon in this manner exerts some gentle pressure on the inside of the nasal wall, helping to control nasal exudation. At the same time, the balloon seals the nostril to prevent further exudation. Any exudates oozing out around the balloon 26 will be absorbed by the absorber 19 arranged around the body 7; additionally, the absorber 33 constituting the tip section 9 will absorb any exudates otherwise accumulating inside of the nasal cavity. Naturally, if the device is to be used to stop nose bleed, it is conceivable to provide a vasoconstricting agent in the absorber sections.

As long as the exudation continues, the front line of the exudate absorbed by the proximally arranged absorber 19 will move along the length of the scale 21 on the shaft, as indicated in FIG. 3. The stalling of this progress would thus indicate ceasing of exudation. To the end of more easily monitoring the progress of the exudates, parts of the shaft may be made of a transparent, preferably polymeric, material. The scale may be formed as a series of equidistant protrusions or marks on the otherwise uniform outer surface of the shaft. A transparent lengthwise strip is sufficient for this purpose, whereas the remainder of the outer surface may be opaque.

In order for the cooling agent 29 to perform its function, it should have a positive enthalpy of solution in the fluid 15. I.e., under normal conditions and constant pressure, the dissolving shall readily take place, but shall require input of energy into the solution. The required energy will be provided by the thermal energy of the solvent and solute. The process will thus lead to internal cooling of the solution and therefore of the balloon 26 as a whole. Via the thin envelope of the balloon 26, the inside of the nasal cavity will likewise be cooled, and exudation will be slowed or stopped. Similarly, any swelling of the nose will be reduced.

It may be estimated that an enthalpy of dissolution of more than 10 kJ/mol may be required to achieve sufficient cooling. Herein, it is assumed that an amount of between 0.1 g and 1 g of the cooling agent 29 may be suitably accommodated in the chamber.

While the invention has been described above in the context of specific embodiments, the skilled person will become aware of various suitable modifications and variations. The above description accordingly shall not be construed as limiting for the invention, which is defined by the appended claims only.

The invention claimed is:

1. An inflatable device for insertion into a user's nose for controlling nasal exudation, the device comprising:
    an elongated shaft including at least one lumen accommodating a liquid;
    an inflatable balloon distally connected to the shaft, the balloon being in fluid connection to the lumen; and
    an absorber configured for absorbing nasal exudates, the absorber being disposed at an outer circumference of the shaft and comprising a section disposed in a portion of the device which remains visible when the device is in use, wherein the shaft bears at least one mark adjacent said visible section, for indicating an amount of nasal exudate absorbed;
    wherein the balloon is configured to seal the nostrils when inflated.

2. The inflatable device for insertion into a user's nose for controlling nasal exudation according to claim 1, the device further comprising:
    another absorber configured for absorbing nasal exudates, the other absorber being disposed at a distal tip portion of the device.

3. The device according to claim 2, wherein the distal tip of the device is entirely made up of the other absorber and a support structure for the other absorber.

4. The device according to claim 2, wherein a length of a distal portion of the device including the inflatable balloon and the distal tip portion does not exceed 5 cm.

5. The device of claim 1, the balloon including absorbing particles on its outer surface.

6. The device of claim 1, wherein at least the shaft and the balloon are separately provided, and are adapted to be assembled before use by a user.

7. An inflatable device for insertion into a user's nose for controlling nasal exudation, the device comprising:
    an elongated shaft including at least one lumen accommodating a liquid; and
    an inflatable balloon connected to the elongated shaft, the balloon being in fluid connection to the lumen, the balloon containing a cooling agent soluble in the liquid, whereby the cooling agent is configured to cool the balloon upon coming into contact with and dissolving in the liquid.

8. The device of claim 7, further comprising a valve or rupturable sealing membrane separating the liquid from the cooling agent while the device is not used.

9. The device of claim 8, further comprising a plunger disposed in the shaft, for urging the liquid into the balloon, in particular through the valve or the ruptured membrane.

10. An inflatable device for insertion into a user's nose for controlling nasal exudation, the device comprising:
    an elongated shaft including at least one lumen accommodating a liquid;
    an inflatable balloon distally connected to the shaft, the balloon being in fluid connection to the lumen; and
    an absorber configured for absorbing nasal exudates, the absorber being disposed at an outer circumference of the shaft;
    wherein the balloon is configured to seal the nostrils when inflated, wherein the balloon contains a cooling agent soluble in the liquid, whereby the cooling agent is configured to cool the balloon upon coming into contact with and dissolving in the liquid.

11. The device of claim 10, further comprising a valve or rupturable sealing membrane separating the liquid from the cooling agent while the device is not used.

12. The device of claim 10, further comprising a plunger disposed in the shaft, for urging the liquid into the balloon, in particular through the valve or the ruptured membrane.

13. A device for insertion into a user's nose for controlling nasal exudation, the device comprising:
    a body section configured to hold and to supply a liquid, and to support an absorber; and
    a balloon section connected to the body portion such that to be inserted first in a user's nose, the balloon section being configured to receive the liquid from the body portion, and housing a balloon that expands upon receiving the liquid thereby sealing the user's nose,
    wherein the absorber surrounds the body section in a portion of the body section adjacent to the balloon section,
    wherein the absorber is partially disposed between a lumen of the body section, the lumen being configured to hold the liquid, and an outer wall of the body section, the outer wall having at least a transparent portion with a scale that remains visible when the device is inserted in the user's nose, thereby enabling to monitor an amount of nasal exudation accumulated in the absorber.

14. The device of claim 13, further comprising a tip absorber mounted on the balloon section opposite to the body section.

15. The device of claim 13, further comprising a valve or rupturable sealing membrane configured to prevent the liquid from entering the balloon prior to the device being inserted into the user's nose.

16. The device of claim 13, wherein the body section and the balloon section are configured to be assembled via mating elements.

17. A device for insertion into a user's nose for controlling nasal exudation, the device comprising:
    a body section configured to hold and to supply a liquid, and to support an absorber; and
    a balloon section connected to the body portion such that to be inserted first in a user's nose, the balloon section being configured to receive the liquid from the body portion, and housing a balloon that expands upon receiving the liquid thereby sealing the user's nose,
    wherein the absorber surrounds the body section in a portion of the body section adjacent to the balloon section,
    wherein a cooling agent, which is soluble in the liquid, is placed inside the balloon to cool the balloon when the cooling agent is dissolved in the liquid.

\* \* \* \* \*